United States Patent
Ichiba et al.

(10) Patent No.: US 10,288,547 B2
(45) Date of Patent: May 14, 2019

(54) FACILITY STATE ANALYSIS DEVICE, ANALYSIS METHOD FOR FACILITY STATE, STORAGE MEDIUM, AND FACILITY MANAGEMENT SYSTEM

(71) Applicant: Tokyo Electric Power Company Holdings, Incorporated, Tokyo (JP)

(72) Inventors: Mikiyuki Ichiba, Tokyo (JP); Tamotsu Uduki, Tokyo (JP); Hideo Mizuochi, Tokyo (JP); Yuya Niidome, Tokyo (JP); Masaomi Takaoka, Tokyo (JP); Shinsuke Nasukawa, Tokyo (JP); Yuuji Tagawa, Tokyo (JP); Hideaki Sato, Tokyo (JP); Yoshiki Sakamoto, Tokyo (JP); Akihiko Kataoka, Tokyo (JP)

(73) Assignee: Tokyo Electric Power Company Holdings, Incorporated, Tokyo (JP)

( * ) Notice: Subject to any disclaimer, the term of this patent is extended or adjusted under 35 U.S.C. 154(b) by 46 days.

(21) Appl. No.: 15/460,777

(22) Filed: Mar. 16, 2017

(65) Prior Publication Data
US 2017/0184488 A1 Jun. 29, 2017

Related U.S. Application Data

(63) Continuation-in-part of application No. PCT/JP2014/081761, filed on Dec. 1, 2014.

(51) Int. Cl.
*G01N 17/00* (2006.01)
*G05B 23/02* (2006.01)
(Continued)

(52) U.S. Cl.
CPC ........... *G01N 17/006* (2013.01); *G01N 21/94* (2013.01); *G01R 31/027* (2013.01);
(Continued)

(58) Field of Classification Search
CPC .. G01N 17/006; G01N 21/94; G01N 2201/12; G05B 23/0272; G01R 31/027;
(Continued)

(56) References Cited

U.S. PATENT DOCUMENTS 9,546,797 B2 * 1/2017 Kuroiwa .................. F24F 11/30
2002/0059075 A1 * 5/2002 Schick ................ B61L 27/0094
701/31.4

FOREIGN PATENT DOCUMENTS

JP H09-97260 A 4/1997
JP 2003-169415 A 6/2003
(Continued)

OTHER PUBLICATIONS

International Search Report dated Feb. 10, 2015 for PCT/JP2014/081761.
Office Action dated Jul. 5, 2016 for JP 2016-514187.

*Primary Examiner* — Bryan Bui
(74) *Attorney, Agent, or Firm* — Drinker Biddle & Reath LLP

(57) ABSTRACT

A facility state analysis device of an embodiment is provided. The device includes an inputter which accepts input of information specifying a state and location of a facility installed outdoors, a calculator which calculates, by performing statistical processing based at least in part on the information specifying the state and location input to the inputter and information on a predetermined section on a map, an average failure year of the facilities in the section, and a display controller which displays, on a display, the average failure year calculated by the calculator superimposed on the map.

8 Claims, 15 Drawing Sheets

(51) Int. Cl.
- *G01N 21/94* (2006.01)
- *G01R 31/02* (2006.01)
- *G06T 7/00* (2017.01)
- *G06T 11/20* (2006.01)
- *G06T 11/60* (2006.01)

(52) U.S. Cl.
CPC ..... *G05B 23/0272* (2013.01); *G01N 2201/12* (2013.01); *G06T 7/0008* (2013.01); *G06T 11/206* (2013.01); *G06T 11/60* (2013.01); *G06T 2207/30136* (2013.01)

(58) Field of Classification Search
CPC ..... G06T 11/60; G06T 11/206; G06T 7/0008; G06T 2207/30136
See application file for complete search history.

(56) References Cited

FOREIGN PATENT DOCUMENTS

| | | |
|---|---|---|
| JP | 2006-321277 A | 11/2006 |
| JP | 2007-135349 A | 5/2007 |
| JP | 2007-263923 A | 10/2007 |
| JP | 2012-13673 A | 1/2012 |
| JP | 2012-13674 A | 1/2012 |
| JP | 2012-251846 A | 12/2012 |
| JP | 2013-89186 A | 5/2013 |

\* cited by examiner

FIG. 2

| ID | TYPE | LOCATION (LATITUDE/LONGITUDE) | SECTION | PERIOD |
|---|---|---|---|---|
| 0001 | TRANSFORMER | (35.2735, 139.5932) | 0156 | 5 YEARS |
| 0002 | TRANSFORMER | (35.3106, 140.0717) | 0156 | 3 YEARS |
| 0003 | TRANSFORMER | (35.1535, 140.0109) | 0158 | 10 YEARS |
| ⋮ | ⋮ | ⋮ | ⋮ | ⋮ |
| 0237 | SWITCH | (35.3001, 139.8123) | 0156 | 8 YEARS |
| 0238 | SWITCH | (34.5727, 139.5113) | 0157 | 0.5 YEARS |
| ⋮ | ⋮ | ⋮ | ⋮ | ⋮ | even
FACILITY STATE ANALYSIS DEVICE, ANALYSIS METHOD FOR FACILITY STATE, STORAGE MEDIUM, AND FACILITY MANAGEMENT SYSTEM

BACKGROUND

Technical Field

Embodiments of the present invention generally relate to a facility state analysis device, analysis method for facility state, storage medium, and facility management system.

Related Art

JP 2013-89186 A discloses a device for detecting a state of power facilities which detects a state of power facilities and displays a detection result on a display.

Power facilities may fail under the influence of the environment. For example, power facilities installed near a coast may fail due to salt damage.

As a specific example, power facilities such as a transformer have a metal housing and thus may have occurrence of rust in the metal housing thereof due to humidity, salt or the like when exposed to the open air outdoors. The power facility is deteriorated over time due to occurrence of rust, thereby damaging durability of the power facilities.

Therefore, in order to prevent occurrence of rust, a metal housing of power facilities is applied with rust prevention treatment. Specifically, the metal housing of transformers is applied with rust prevention processing such as painting or plating. However, when the painting or plating of power facilities is detached due to long-term use, rust occurs in a detached part. A worker confirms a state of rust of the power facility having rust occurrence. When an amount of rust is large and corrosion is progressing, the worker discards the power facility.

However, there are cases where the degree of failure of a power facility under the influence of the environment is not clear and thus it is difficult to take a concrete countermeasure. Moreover, there are similar cases with facilities other than power facilities.

SUMMARY

A facility state analysis device may include, but is not limited to, an inputter which accepts input of information specifying a state and location of a facility installed outdoors, a calculator which calculates, by performing statistical processing based at least in part on the information specifying the state and location input to the inputter and information on a predetermined section on a map, an average failure year of the facilities in the section, and a display controller which displays, on a display, the average failure year calculated by the calculator superimposed on the map.

BRIEF DESCRIPTION OF THE DRAWINGS

FIG. 2 is a diagram representing exemplary power facility information stored in a power facility information storage.

DETAILED DESCRIPTION OF THE EMBODIMENTS

Figure 1:
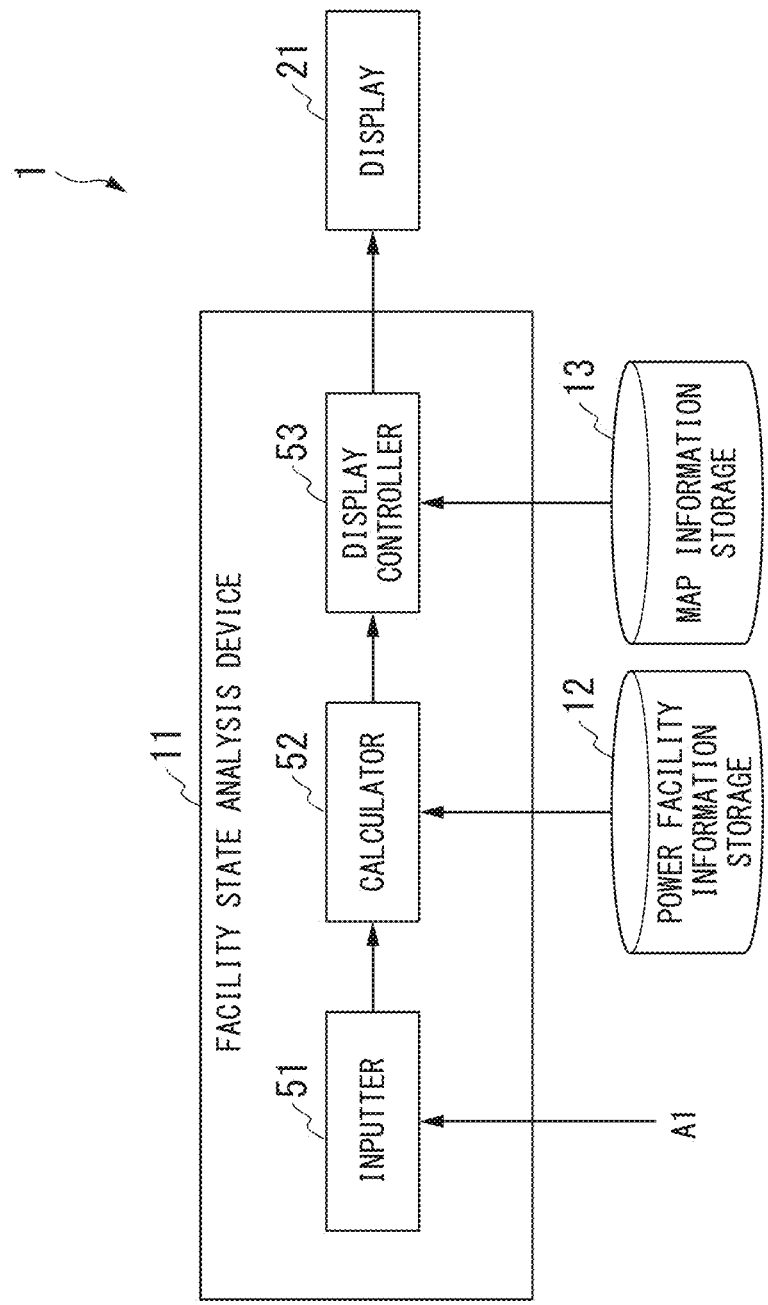
FIG. 1 is a diagram representing a configuration of a power facility management system including a facility state analysis device according to a first embodiment.

A facility state analysis device may include, but is not limited to, an inputter which accepts input of information specifying a state and location of a facility installed outdoors, a calculator which calculates, by performing statistical processing based at least in part on the information specifying the state and location input to the inputter and information on a predetermined section on a map, an average failure year of the facilities in the section, and a display controller which displays, on a display, the average failure year calculated by the calculator superimposed on the map.

In the facility state analysis device, the inputter includes an image analyzer which analyzes an image of the facility and acquires the information on the state of the facility.

The facility state analysis device may include, but is not limited to, a remaining life calculator which calculates a remaining life of the facility and performs notification based at least in part on the calculated remaining life.

The facility state analysis device may include, but is not limited to, a section generator which generates a section based at least in part on the information accepted by the inputter.

In the facility state analysis device, the information specifying the location of the facility is an ID of the facility and the inputter acquires location information associated with the ID of the facility based at least in part on association information of the ID and location of the facility.

In the facility state analysis device, the display is a display of a terminal device.

In the facility state analysis device, the display controller classifies the average failure year into a predetermined number of ranges and displays, on the display, the average failure year superimposed on the map.

In the facility state analysis device, the display controller displays, on the display, the average failure year superimposed on the map for each of regions smaller than the section.

In the facility state analysis device, the display controller displays, on the display, a distance from a coast superimposed on the map.

In the facility state analysis device, the display controller accepts selection of a specific type from among a plurality of types of facilities.

In the facility state analysis device, the facility is a power facility.

An analysis method for facility state may include, but is not limited to, accepting input of information specifying a state and location of a facility installed outdoors, calculating, by performing statistical processing based at least in part on the accepted information specifying the state and location and information on a predetermined section on a map, an average failure year of the facilities in the section, and displaying, on a display, the calculated average failure year superimposed on the map.

A non-transitory computer-readable storage medium storing a program, when executed by a computer, to cause a computer to execute accepting input of information specifying a state and location of a facility installed outdoors, calculating, by performing statistical processing based at least in part on the accepted information specifying the state and location and information on a predetermined section on a map, an average failure year of the facilities in the section, and displaying, on a display, the calculated average failure year superimposed on the map.

A facility management system may include, but is not limited to, a facility state analysis device and a display, where the facility state analysis device includes an inputter which accepts input of information specifying a state and location of a facility installed outdoors, a calculator which calculates, by performing statistical processing based at least in part on the information specifying the state and location input to the inputter and information on a predetermined section on a map, an average failure year of the facilities in the section, and a display controller which displays, on the display, the average failure year calculated by the calculator superimposed on the map.

A facility state analysis device, analysis method for facility state, storage medium, and facility management system may allow for implementing display on a map for easy recognition of an average failure year representing the degree of failure of a facility such as a power facility under the influence of the environment.

The term "facility" used in embodiments refers to every tangible thing, which can in generally be designed, constructed, built, manufactured, installed, and maintained for performing any purpose, activities or functions in human society. In some cases, the facility may include, but is not limited to, a permanent, semi-permanent or temporary commercial or industrial property such as building, plant, or structure for performing any purpose, activities or functions in human society.

The term "event" used in embodiments refers to something that happens such as a social occasion or activity.

The term "equipment" used in embodiments refers to a set of one or more tangible articles or physical resources such as, but not limited to, some structural or tangible elements, apparatus, devices, or implements used in an operation or activity; fixed assets other than land and buildings.

The term "equipment/material" used in embodiments refers to at least one of equipment and material, for example, equipment alone, material alone or in combination. Hereinafter, embodiments of a facility state analysis device, analysis method for facility state, storage medium, and power facility management system will be described with reference to the drawings.

(First Embodiment)

FIG. 1 is a diagram representing a configuration of a power facility management system 1 including a facility state analysis device 11.

The power facility management system 1 includes the facility state analysis device 11, a power facility information storage 12, map information storage 13, and display 21.

The power facility information storage 12 stores power facility information.

FIG. 2 is a diagram representing exemplary power facility information stored in the power facility information storage 12. The power facility information storage 12 may be, for example, a data base.

Power facility information represented in FIG. 2 includes identification (ID) information of a power facility, type information, location information, section information, and period information associated thereamong. In the present embodiment, the ID is numerical information and the type information is information on the name of the power facility. The location information is information on latitude and longitude. The section information includes numerical information representing each of the sections and information on a range specifying each of the sections. The period information is information on a period of time (operation period) elapsed from installation of the power facility. The ID may be, for example, one or both of a model number and serial number. The information specifying a section may be, for example, information specifying a range with latitude and longitude.

As the types of power facilities, various information may be used such as types of equipment of power facilities (e.g. name of a power facility). Moreover, types of size or length of the power facility may be used as well as the type of equipment of power facilities. Incidentally, the types of equipment may include types of materials. Also, the types may be referred to as kinds.

As the sections, various sections may be used. As an example, sections of distribution blocks in the units of members used in management or the like may be used. As another example, sections based at least in part on postal codes may be used.

Incidentally, information stored in the power facility information is not limited to the examples in FIG. 2 but may be various information. Also, forms of each piece of information may be various forms such as using the form of numbers as for the IDs. Moreover, in the present embodiment, the same sections are used for all types of power facilities; however, different sections may be used for each of the types. Furthermore in the present embodiment, the power facility information includes information on a plurality of different types of power facilities; however, separate pieces of power facility information may be provided for each of the types.

In the present embodiment, the power facility information storage 12 is provided externally to the facility state analysis device 11; however, the power facility information storage 12 may be provided therein.

The map information storage 13 stores map information. In the present embodiment, the map information storage 13 stores Japanese map information; however, information on another map may be stored therein. The map information storage 13 is, for example, a data base.

Incidentally, the map information storage 13 may be a storage storing map information dedicated to the power facility management system 1 or may be a storage on the Internet storing map information publicly available.

In the present embodiment, the map information storage 13 is provided externally to the facility state analysis device 11; however, the map information storage 13 may be provided therein.

The display 21 is, for example, a display device including a screen (display).

The display 21 may be various articles capable of displaying information on the screen, for example, a display device having a function dedicated to display or a part of a display function integrated to a personal computer.

The facility state analysis device 11 will be described.

The facility state analysis device 11 includes an inputter 51, a calculator 52, and a display controller 53.

The inputter 51 accepts input of information A1. The information A1 specifies a state and location of a power facility installed outdoors. The inputter 51 outputs the accepted input information to the calculator 52.

In the present embodiment, the inputter 51 accepts input of information on a plurality of power facilities for a specific type of power facility. Moreover, in the present embodiment, the inputter 51 includes an operator such as a keyboard and mouse allowing for operation by a user (human) and thereby accepts input according to operation of the operator. The user may be, for example, a worker or the like related to the power facilities.

As a state of a power facility, a state where the power facility is failed or a state where the power facility is not failed is used. Incidentally, of the two pieces of information as to whether the power facility is failed, any one thereof may be used or the both may be used.

As the information specifying the location, location information is used in the present embodiment. As the location information, information on latitude and longitude is used in the present embodiment. The location information is, for example, input by the user.

Incidentally, as the information on the power facility, for example, information obtained by examining the power facility installed outdoors may be used. Alternatively, the power facility installed outdoors may be removed and information obtained by examining the removed power facility (removed article) may be used.

The calculator 52 calculates, by performing statistical processing based at least in part on the information specifying the state and location input to the inputter 51 and information on a predetermined section on a map, an average failure year of the power facilities in the section. The calculator 52 outputs, to the display controller 53, section information and information on the average failure year of the power facilities in the section for each of the sections.

In the present embodiment, the sections are predetermined on the Japanese map. Furthermore, each of the power facilities are associated with information on a section (section data) to which a place installed with each of the power facilities belongs. The calculator 52 acquires, for the power facility for which the information specifying the state and location has been input from the inputter 51, section information associated with the location and operation period information based at least in part on the power facility information stored in the power facility information storage 12. Thereafter, the calculator 52 outputs, to the display controller 53, information on each of the sections and information on the average failure year of the power facilities in each of the sections for a specific type of power facility.

As the statistical processing, in the present embodiment, processing of Weibull analysis is used for the plurality of power facilities of the specific type. As the statistical processing, other various processing may be used and, for example, processing using a histogram may be used.

The display controller 53 displays, on the display 21, the average failure year calculated by the calculator 52 superimposed on the map.

In the present embodiment, the display controller 53 acquires Japanese map information based at least in part on map information stored in the map information storage 13 and acquires information on each of the sections and information on the average failure year for a specific type of power facility based at least in part on the information input from the calculator 52. Thereafter, the display controller 53 generates, on the map, display information representing each of the sections and the average failure year based at least in part on the acquired information and outputs the display information to the display 21. This allows for the display 21 to display the display information on a screen according to control information (display information in the present embodiment) from the display controller 53.

Here, as another exemplary configuration, information on ranges specifying each of the sections may not be included in the power facility information but association between numeral information representing each of the sections and information on ranges specifying each of the sections may be stored in any storage as association information other than the power facility information or map information. In this case, the calculator 52 acquires, for each of the power facilities, section information (numerical information representing each of the sections and information on ranges specifying each of the sections) based at least in part on the power facility information and association information thereof.

Moreover, as another exemplary configuration, information on ranges specifying each of the sections may not be included in the power facility information but association between numeral information representing each of the sections and information on ranges specifying each of the sections may be stored in the map information storage 13 while included in the map information. In this case, the calculator 52 uses, as the section information, the numerical information representing each of the sections and the display controller 53 then acquires, for each of the power facilities, information on ranges specifying each of the sections associated with the numerical information representing each of the sections based at least in part on the map information.

Moreover, in the present embodiment, the inputter 51, calculator 52, and display controller 53 process information on, for example, power facilities of one specific type; however, as another exemplary configuration, information of power facilities of a plurality of different types may be processed for each of the types. As still another exemplary configuration, the inputter 51, calculator 52, and display controller 53 may handle information of power facilities of two or more different types in a similar manner and process the information at a time.

Figure 3:
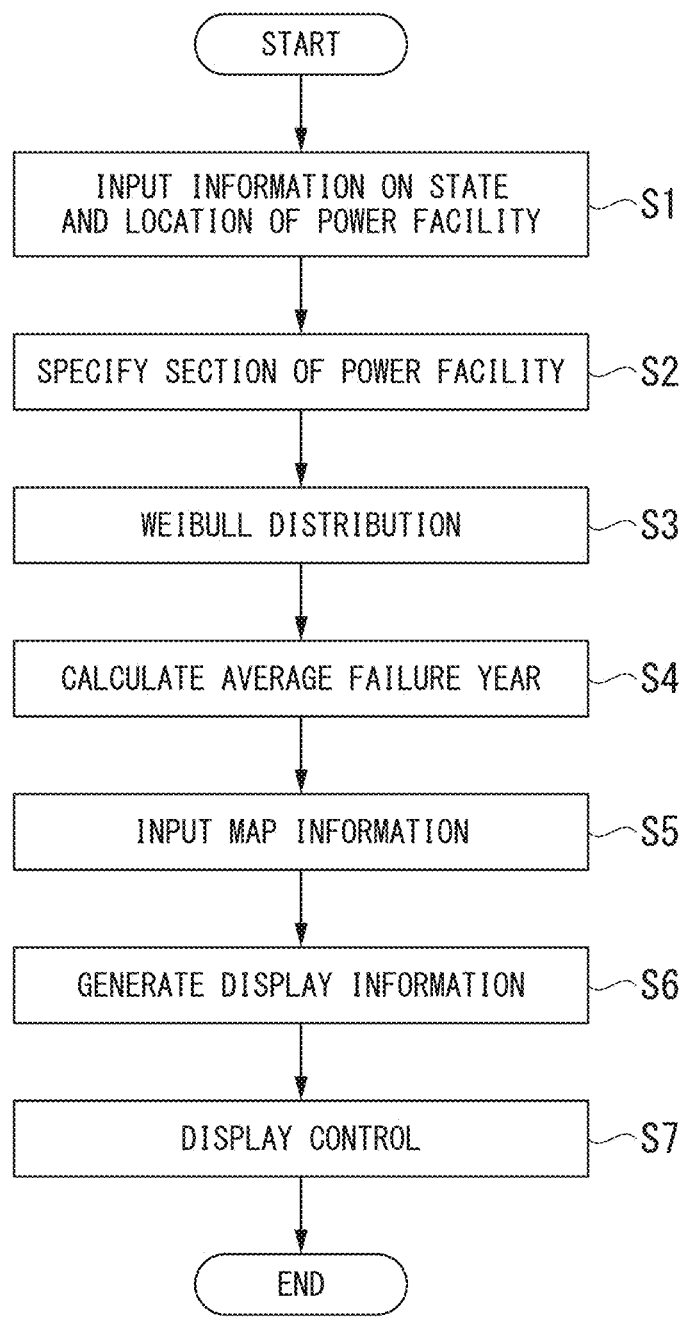
FIG. 3 is a flowchart representing an exemplary procedure of processing performed in the facility state analysis device.

FIG. 3 is a flowchart representing an exemplary procedure of processing performed in the facility state analysis device 11.

First, the inputter 51 accepts input of information on a state and location of power facilities (step S1). Next, the calculator 52 specifies sections of the power facilities based at least in part on the information accepted by the inputter 51 and power facility information (step S2). Next, the calculator 52 performs Weibull analysis on the power facilities of a specific type for each of the specified sections (step S3). Next, the calculator 52 calculates the average failure year for the specific type of power facility based at least in part on a result of the Weibull analysis (step S4). Next, the display controller 53 inputs map information thereto (step S5). Next, the display controller 53 generates display information based at least in part on information obtained by the calculator 52 and the map information (step S6). Thereafter, the display controller 53 performs display control and displays the generated display information on the display 21 (step S7).

Figure 4:
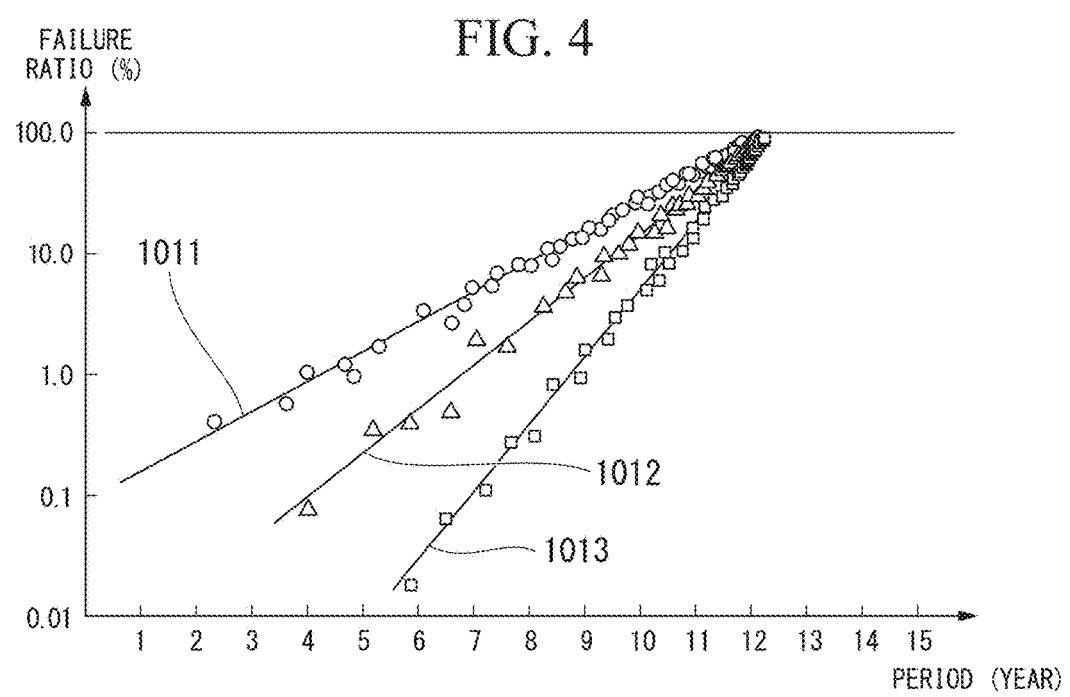
FIG. 4 is a diagram representing an exemplary result of Weibull analysis.

FIG. 4 is a diagram representing an exemplary result of Weibull analysis.

In the graph represented in FIG. 4, a horizontal axis represents period (e.g. years) while a vertical axis represents failure ratio (%). As the period, an operation period is used.

In the example in FIG. 4, the result of Weibull analysis is represented for three different sections. In the present embodiment, these sections are referred to as a first section, second section, and third section.

As the result of Weibull analysis, a linear line 1011 was obtained for the power facilities of the specific type based at least in part on information on a plurality of power facilities included in the first section. Similarly, a linear line 1012 was obtained based at least in part on information on a plurality of power facilities included in the second section. Similarly, a linear line 1013 was obtained based at least in part on information on a plurality of power facilities included in the third section. The specific type may be, for example, a transformer or the like.

The calculator 52 calculates the average failure year of the power facilities in each of the sections based at least in part on the linear lines 1011 to 1013 in each of the sections. In the example in FIG. 4, the average failure year decreases in the order of the first section (linear line 1013), second section (linear line 1012), and third section (linear line 1013).

Figure 5:
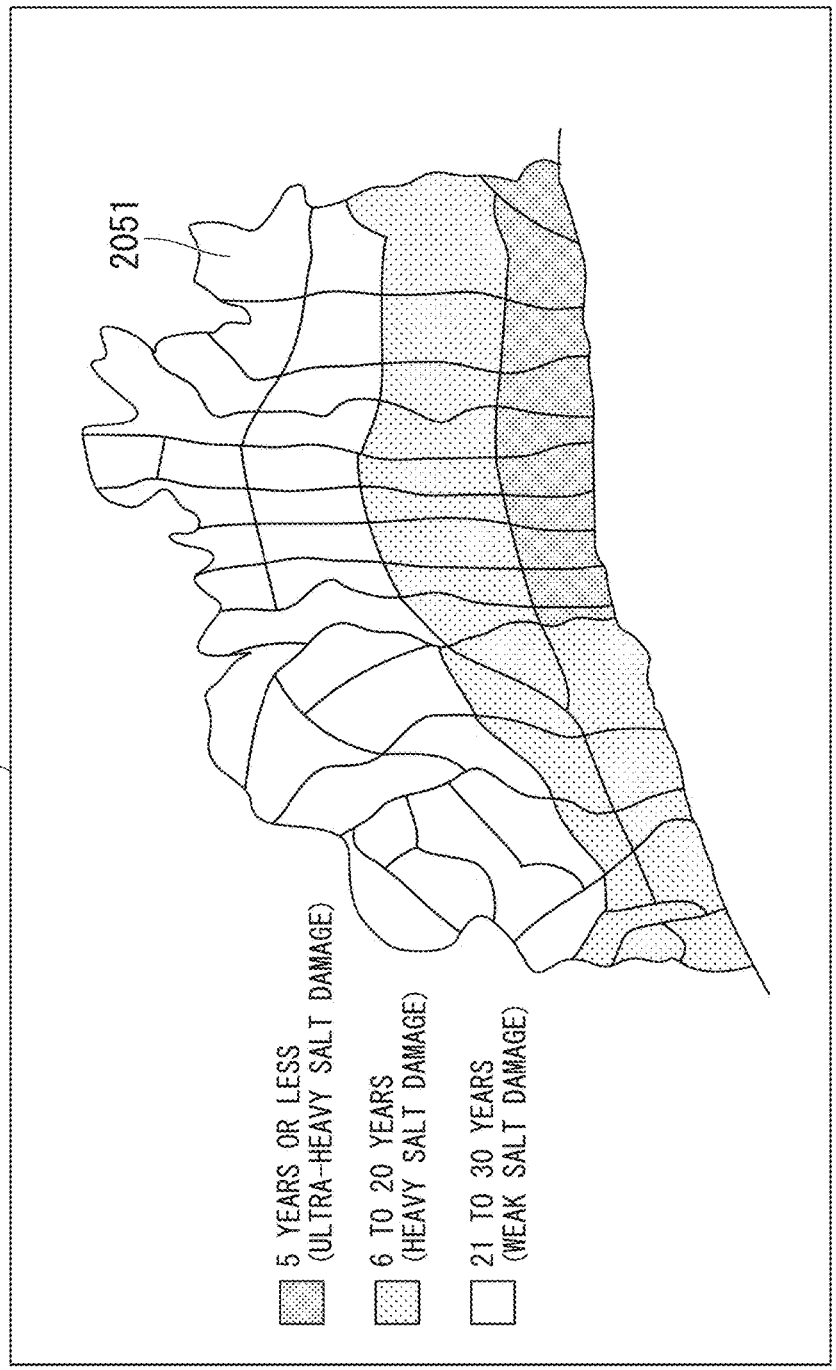
FIG. 5 is a diagram representing exemplary display information displayed on a screen of a display.

FIG. 5 is a diagram representing an example of display information displayed on a screen 2011 of the display 21.

In the example of display information on the screen 2011, a plurality of sections is overwritten on a map of a particular region in Japan (e.g. Kanagawa pref.). For each of the sections, the average failure year is further represented for a specific type of power facility. In the example in FIG. 5, of the plurality of sections, only one section 2051 is denoted with a symbol. The specific type may be, for example, a transformer or the like.

In the example in FIG. 5, the display controller 53 generates display information which displays the average failure years in the plurality of sections classified into three ranges. Specifically, the display controller 53 classifies the average failure years in the plurality of sections into the three ranges including a range of five years or less of average failure year (range assumed as ultra-heavy salt damage), a range of six to twenty years of average failure year (range assumed as heavy salt damage), and a range of 21 to 30 years of average failure year (range assumed as weak salt damage). Thereafter, the display controller 53 generates display information which displays the average failure year in the plurality of sections in three different colors for each of the ranges to which each of the sections belong.

Incidentally, a period between five years and six years may be included in any one of the ranges of 5 years or less and six to twenty years. In a similar manner, a period between 20 years and 21 years may be included in any one of the ranges of six to twenty years and 21 to 30 years.

In the example in FIG. 5, the display controller 53 classifies the average failure years into a predetermined number of ranges (e.g. two or more) and displays, on the display 21, the average failure year superimposed on the map.

In the example in FIG. 5, it is possible to grasp a result of classification, into a predetermined number of ranges, of the average failure year for each of the sections. This allows for, for example, optimizing a design criteria of a power facility to be installed for each of the classified ranges.

Incidentally, a method of displaying the average failure year in the plurality of sections may be a different method. For example, a method to display a value of the average failure year for each of the sections, a method to display all different average failure years allotted with different colors, or a method to display using ranges of average failure years, the number of ranges other than three. Alternatively, patterns may be used instead of colors.

Figure 6:
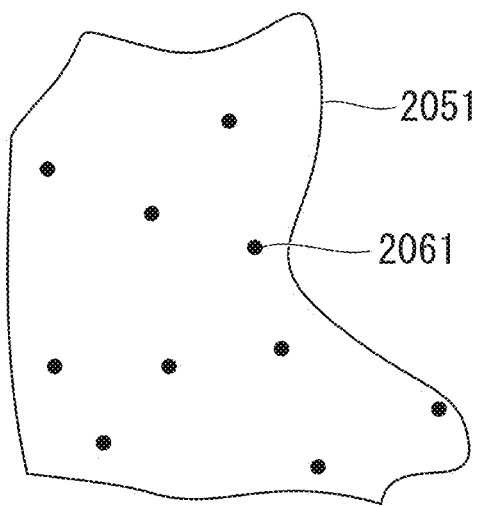
FIG. 6 is a diagram representing exemplary arrangement of power facilities included in one section.

FIG. 6 is a diagram representing exemplary arrangement of power facilities included in the section 2051.

In the example in FIG. 6, each of the plurality of power facilities existing at locations included in the section 2051 is represented by a dot. Only one power facility 2061 from among the plurality of power facilities is denoted with a symbol. The power facility is, for example, a transformer.

The facility state analysis device 11 according to the present embodiment includes the inputter 51 which accepts input of information specifying a state and location of a power facility installed outdoors, the calculator 52 which calculates, by performing statistical processing based at least in part on the information specifying the state and location input to the inputter 51 and information on a predetermined section on a map, an average failure year of the power facilities in the section, and the display controller 53 which displays, on the display 21, the average failure year calculated by the calculator 52 superimposed on the map.

Also, an analysis method for facility state according to the present embodiment includes the steps of accepting input of information specifying a state and location of a power facility installed outdoors, calculating, by performing statistical processing based at least in part on the accepted information specifying the state and location and information on a predetermined section on a map, an average failure year of the power facilities in the section, and displaying, on a display, the calculated average failure year superimposed on the map.

The power facility management system 1 including the facility state analysis device 11 according to the present embodiment allows for implementing display on a map for easy recognition of the average failure year representing the degree of failure of a power facility under the influence of the environment. The power facility management system 1 according to the present embodiment allows for grasping the average failure year of the power facilities for each of the sections. This allows for, for example, optimizing a design criteria of a power facility to be installed.

Figure 7:
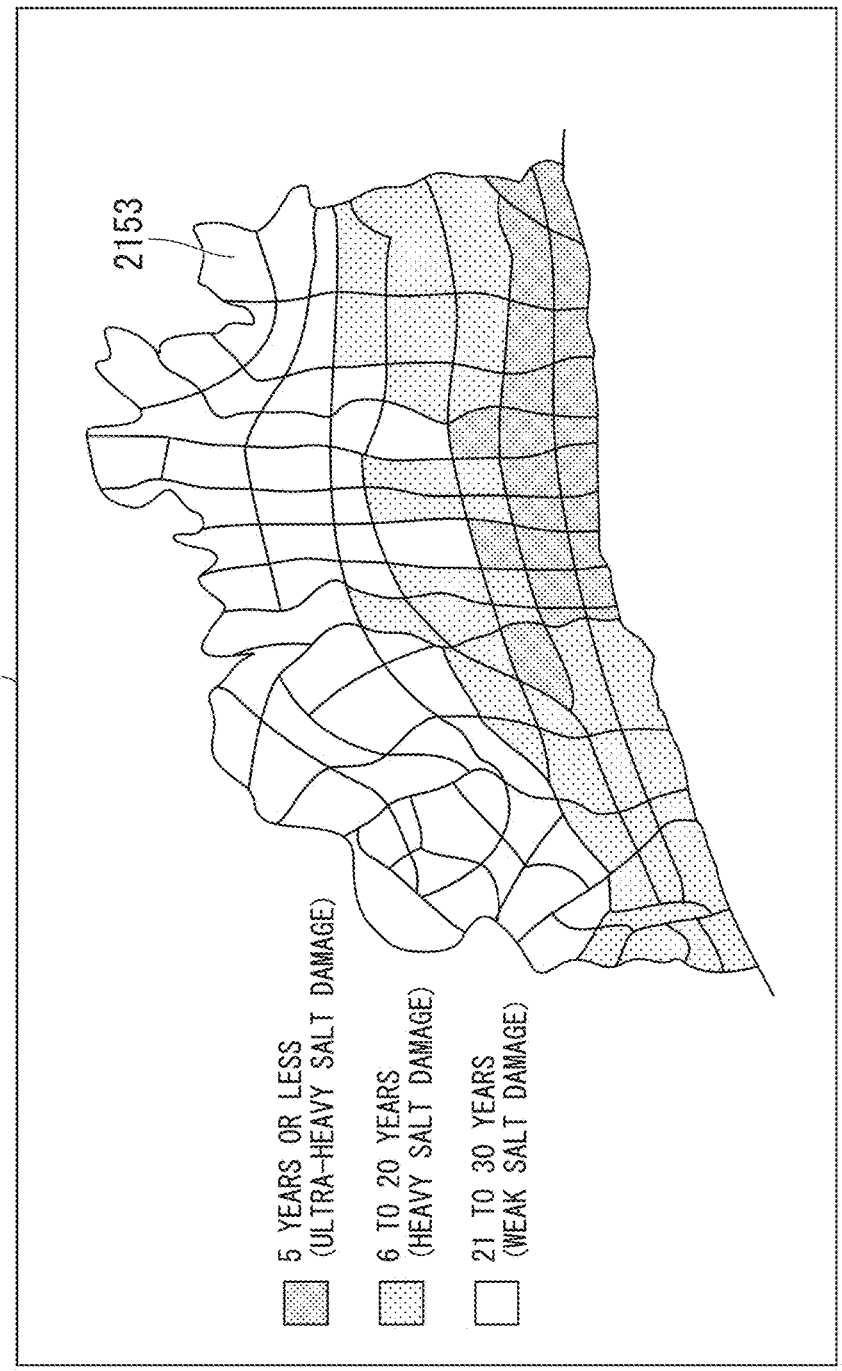
FIG. 7 is a diagram representing another example of display information displayed on a screen of a display.

FIG. 7 is a diagram representing another example of display information displayed on the screen 2011 of the display 21.

In the example of display information on the screen 2011, a plurality of sections is overwritten on a map of a particular region in Japan (e.g. Kanagawa pref.) and a plurality of regions (referred to as divided region in the present embodiment) smaller than a section is further overwritten thereon. For each of the divided regions, the average failure year is further represented for a specific type of power facility. In the example in FIG. 7, of the plurality of divided regions, only one divided region 2153 is denoted with a symbol. The specific type may be, for example, a transformer or the like.

In the example in FIG. 7, the display controller 53 generates display information which displays the average failure years in the plurality of divided regions classified into three ranges.

Here information specifying the divided region is stored in, for example, the power facility information storage 12 or another storage. The calculator 52 acquires the information from the storage storing the information specifying the divided region and performs Weibull analysis for each of the divided regions based at least in part on the acquired information. That is, in the example in FIG. 7, the calculator 52 performs Weibull analysis using divided regions as units instead of sections and the display controller 53 generates display information using divided regions as units instead of sections.

In the example in FIG. 7, the display controller 53 displays, on the display 21, the average failure year superimposed on the map for each of regions (divided regions) smaller than a section.

In the example in FIG. 7, it is possible to grasp the average failure year of the power facilities for each of the regions (divided regions) smaller than a section. This allows for, for example, optimizing a design criteria of a power facility to be installed for each of the regions smaller than a section.

Figure 8:
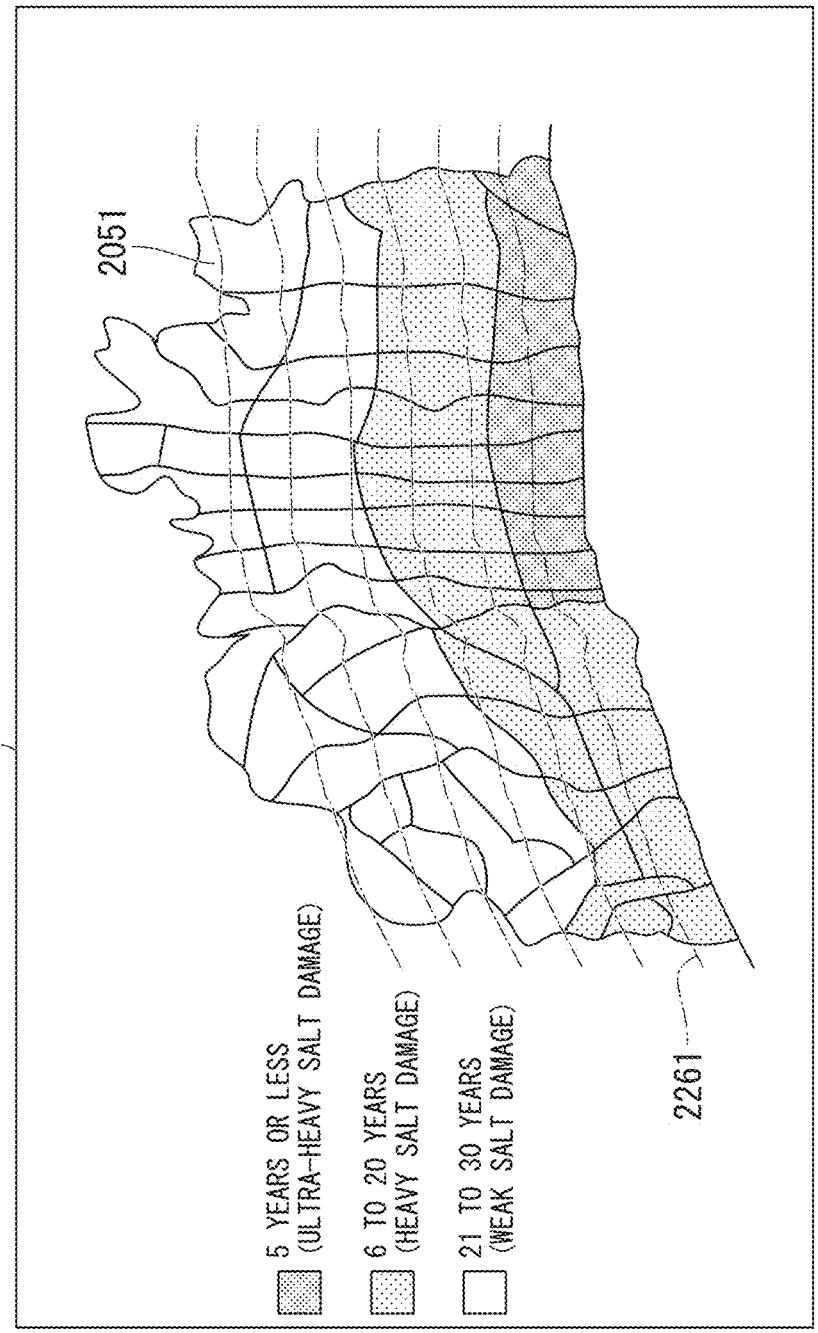
FIG. 8 is a diagram representing still another example of display information displayed on a screen of a display.

FIG. 8 is a diagram representing still another example of display information displayed on the screen 2011 of the display 21.

In the example in FIG. 8, in addition to the same display information as represented in FIG. 5, a line connecting a collection of locations having a predetermined value of a distance from a coast is overwritten on a map and thereby displayed. In the example in FIG. 8, of the plurality of lines representing a distance from the coast, only one line 2261 is denoted with a symbol.

Here, information on the coast is, for example, included in the map information stored in the map information storage 13. The display controller 53 calculates the line, connecting the collection of locations where a predetermined value of distance from the coast is constant, for sections of the land to be displayed as the line representing a distance from the coast based at least in part on the map information and includes the line in the display information.

In the example in FIG. 8, the display controller 53 displays, on the display 21, the distance from the coast superimposed on the map.

In the example in FIG. 8, it is possible to grasp a distribution of the average failure year of the power facilities and distribution of the distance from the coast for each of the sections, thereby allowing for comparison therebetween. This allows for grasping areas where the average failure years due to salt damage (damage caused by salt from the sea) are different even though the distance from the coast is the same. This allows for, for example, optimizing a design criteria of a power facility to be installed.

Figure 9:
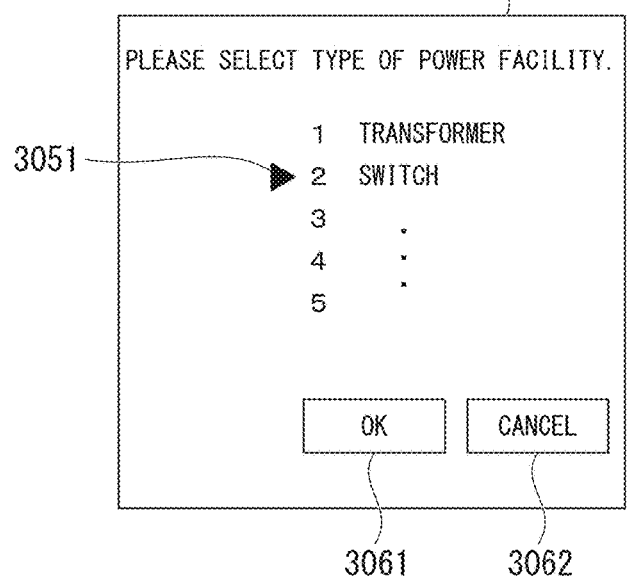
FIG. 9 is a diagram representing an exemplary screen used for selecting a type of power facility.

FIG. 9 is a diagram representing an exemplary screen 2011 used for selecting a type of power facility.

In the example in FIG. 9, the screen 2011 of the display 21 is used; however, a screen of the facility state analysis device 11 or another device may be used.

On the screen 2011 represented in FIG. 9, letters "Please select type of power facility." and letters "1 Transformer 2 Switch 3 . . . (omitted below)" are displayed.

A user can change a display position of a cursor 3051 displayed on the screen 2011 by operating the inputter 51 of the facility state analysis device 11 or an inputter of the other device. Specifically, the display controller 53 generates display information to change the display position of the cursor 3051 displayed on the screen 2011 upon operation by the user.

The user can select a bottom for acceptance (OK bottom 3061) or a bottom for refusal (cancel bottom 3062) displayed on the screen 2011 by operating the inputter 51 of the facility state analysis device 11 or the inputter of the other device. Specifically, the display controller 53 accepts selection of the OK bottom 3061 or the cancel bottom 3062 displayed on the screen 2011 upon operation by the user.

When the cursor 3051 is moved to a position corresponding to a desired type of power facility and the OK bottom 3061 is selected by operation of the user, the display controller 53 accepts selection of the corresponding type of power facility. When the cancel bottom 3062 is selected by operation of the user, display of the screen 2011 represented in FIG. 9 is canceled.

In the facility state analysis device 11, various processing may be performed depending on the type of power facility accepted by the display controller 53.

For example, the calculator 52 may perform Weibull analysis for the accepted type of power facility.

For example, the display controller 53 may generate display information for the accepted type of power facility.

In the example in FIG. 9, the display controller 53 accepts selection of a specific type from among a plurality of types of power facilities.

In the example in FIG. 9, it is possible to select a desired type from among the plurality of types of power facilities. This allows for executing various processing for the power facilities of the desired type.

Figure 10:
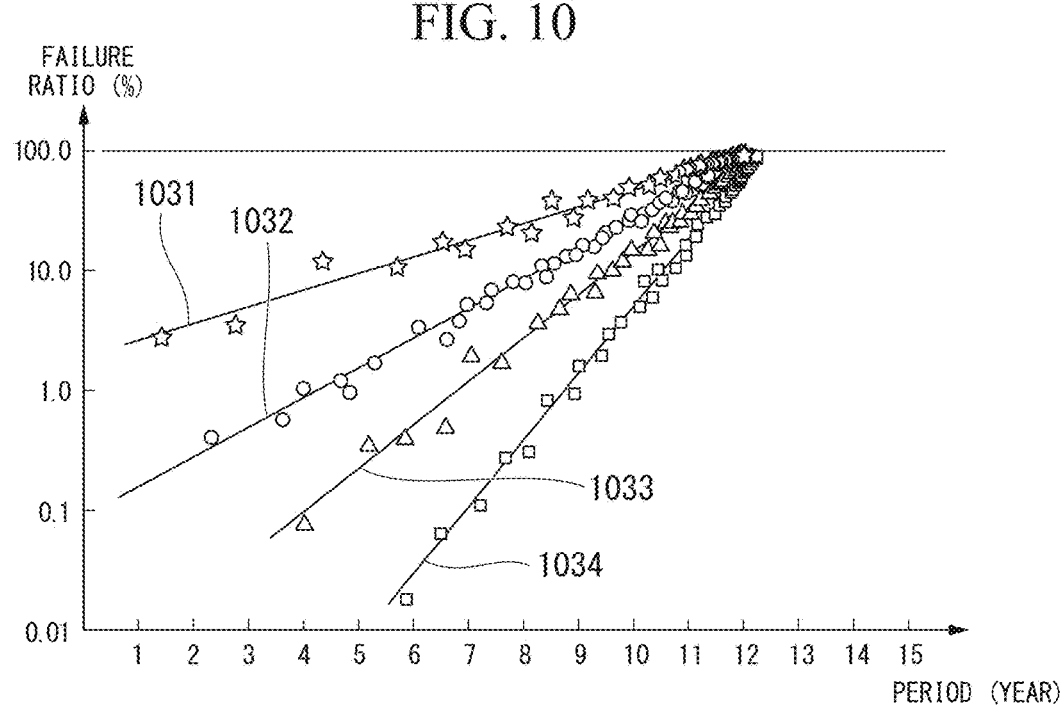
FIG. 10 is a diagram representing another exemplary result of Weibull analysis.

FIG. 10 is a diagram representing another exemplary result of Weibull analysis.

In the graph represented in FIG. 10, a horizontal axis represents period (e.g. years) while a vertical axis represents failure ratio (%).

In the example in FIG. 10, the result of Weibull analysis is represented for four different sections. Respective linear lines 1031 to 1034 were obtained for the respective sections.

In this manner, as a method of Weibull analysis, various methods may be used.

(Second Embodiment)

Figure 11:
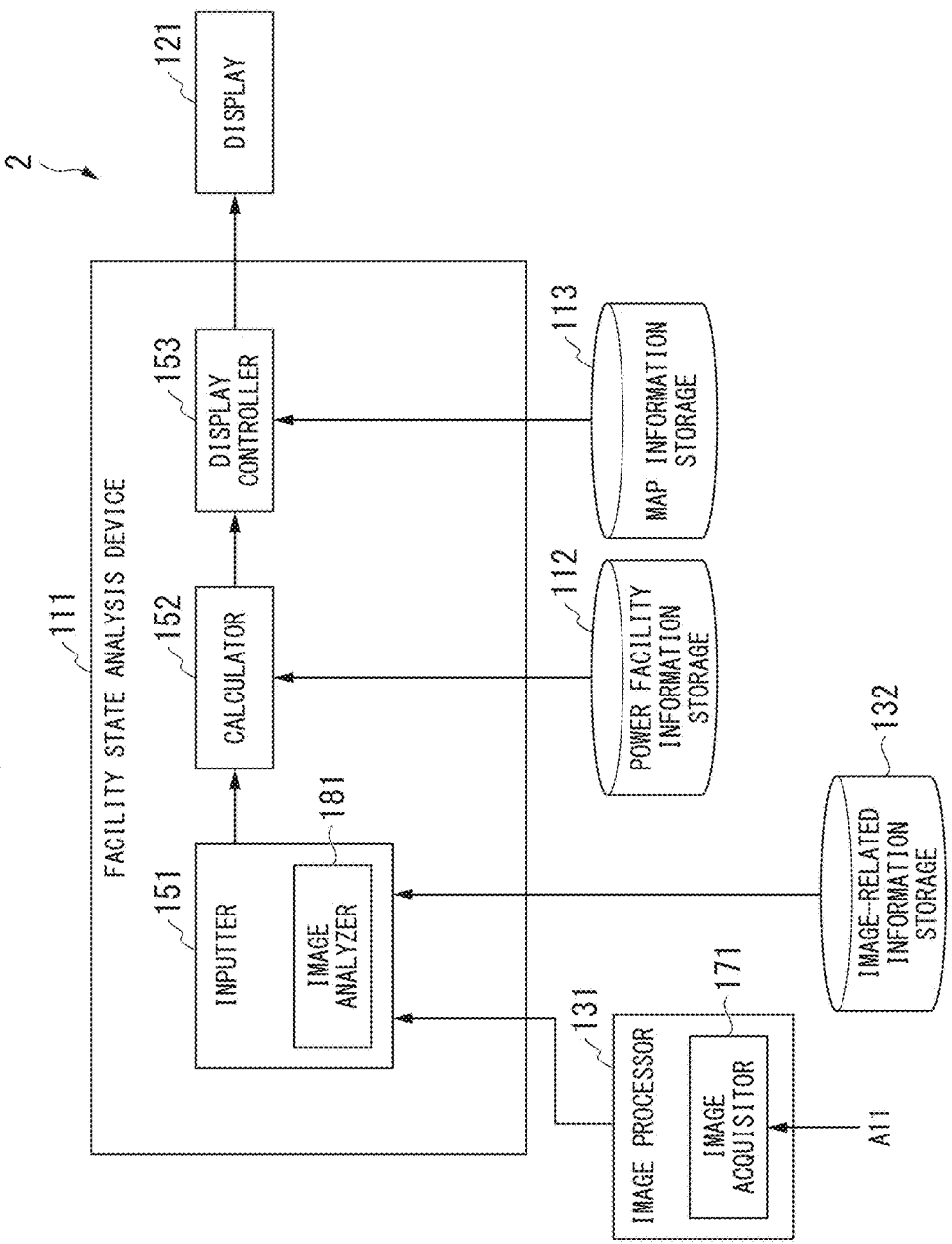
FIG. 11 is a diagram representing a configuration of a power facility management system including a facility state analysis device according to a second embodiment.

FIG. 11 is a diagram representing a configuration of a power facility management system 2 including a facility state analysis device 111.

The power facility management system 2 includes the facility state analysis device 111, a power facility information storage 112, map information storage 113, display 121, image processor 131, and image-related information storage 132.

The facility state analysis device 111 includes an inputter 151, a calculator 152, and a display controller 153.

The inputter 151 includes an image analyzer 181.

Here, a configuration and operations of the power facility management system 2 is the same as those of the corresponding configuration units represented in FIG. 1 except for those related to the image processor 131, image-related information storage 132, and inputter 151. In the present embodiment, therefore, configuration units different from those of the system represented in FIG. 1 will be described in detail.

The image-related information storage 132 stores image-related information used for determination of a state of a power facility based at least in part on an image of the power facility. As the image-related information, image information of all or a part of the power facility in a predetermined state or information on a threshold value for determination as to whether the power facility is in the predetermined state may be used. As the predetermined state, a state where the power facility is failed or a state where the power facility is not failed is used.

The image processor 131 includes an image acquisitor 1711.

The image acquisitor 171 acquires information A11. The information A11 is information of an image of the power facility a state of which is to be determined. The image acquisitor 171 outputs the acquired image information to the facility state analysis device 111. The image acquisitor 17 is, for example, an imaging device which images an image or a device to which information of an imaged image is input.

In the facility state analysis device 111, the inputter 151 accepts input of the image information output from the image acquisitor 171 of the image processor 131. The image analyzer 181 of the inputter 151 analyzes a target power facility represented in the accepted image based at least in part on the accepted image information and the image-related information stored in the image-related information storage 132.

Specifically, the image analyzer 181 determines the state of the target power facility. Thereafter, the image analyzer 181 outputs a determination result of the state of the target power facility and location information of the power facility.

Here, the location information of the power facility is, for example, input to the inputter 151 of the facility state analysis device 111 by the user. Alternatively, the location information of the power facility is input to the image processor 131 by the user and then input to the inputter 151 of the facility state analysis device 111 by the image processor 131.

As another exemplary configuration, when the image acquisitor 171 is an imaging device, the image acquisitor 171 may be provided with a global positioning system (GPS) function and acquire the location information of the power facility by the GPS function when imaging an image of the power facility. In this case, the image acquisitor 171 outputs the acquired location information of the power facility to the inputter 151 of the facility state analysis device 111.

As still another exemplary configuration, a unique ID may be allotted to each of the power facilities and the image analyzer 181 may specify the location information of the power facility based at least in part on the ID captured in the image. For example, association information of the IDs and locations of the power facilities may be included in the image-related information to allow the image analyzer 181 to detect location information associated with the ID of the power facility based at least in part on the association information.

Incidentally, the image analyzer 181 is included in the inputter 151 of the facility state analysis device 111 in the present embodiment. However, as another exemplary configuration, the function of the image analyzer 181 may be included in the image processor 131 without including the image analyzer 181 in the inputter 151 of the facility state analysis device 111 and information obtained by the image analyzer 181 may be output to the inputter 151 of the facility state analysis device 111.

In the facility state analysis device 111 according to the present embodiment, the inputter 151 includes the image analyzer 181 which analyzes an image of the power facility and acquires information on the state of the power facility.

In the power facility management system 2 including the facility state analysis device 111 according to the present embodiment, it is possible to determine the state of the power facility based at least in part on an image of the power facility. Furthermore, a location of the power facility may be determined based at least in part on the image of the power facility.

(Third Embodiment)

Figure 12:
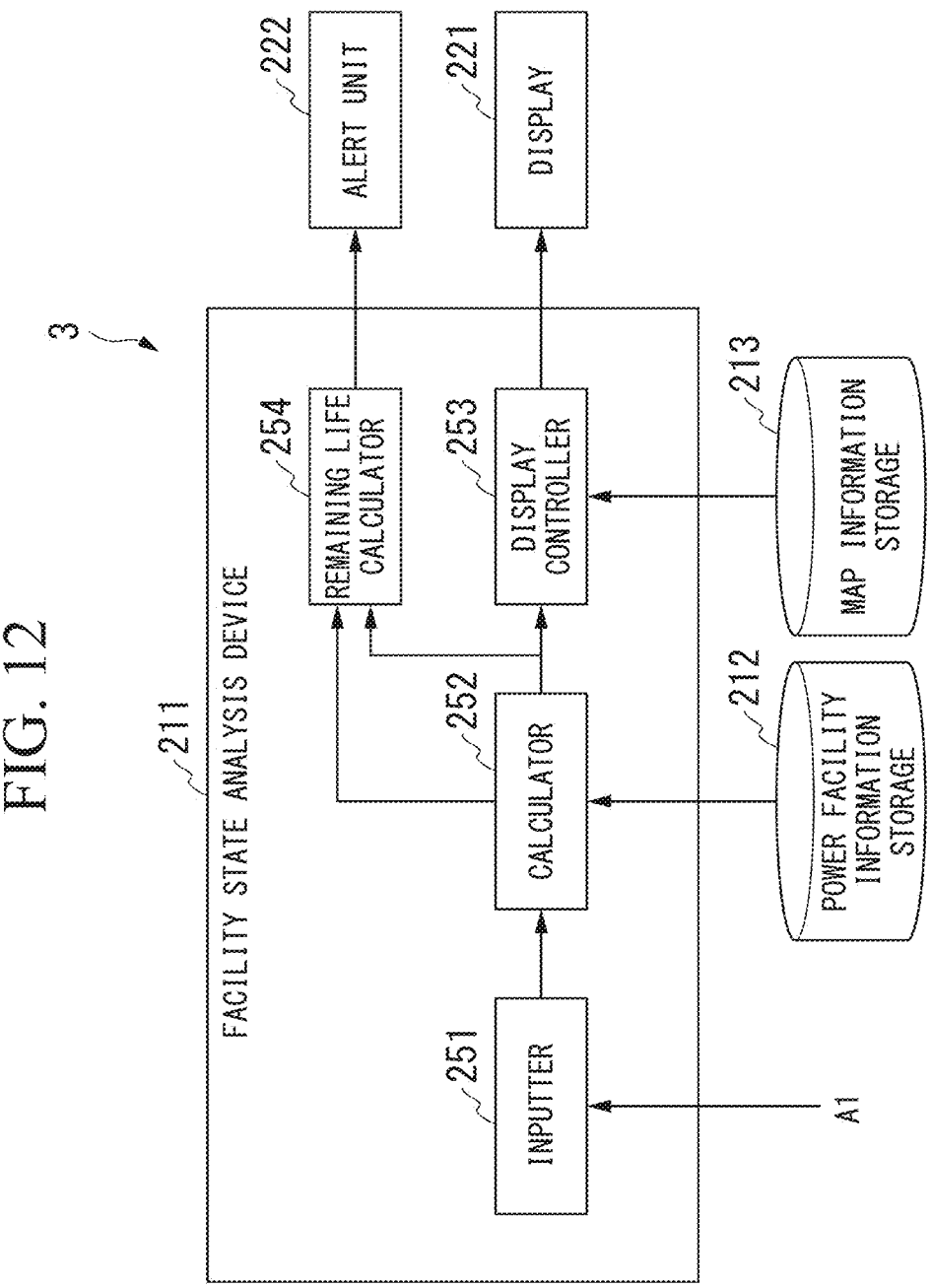
FIG. 12 is a diagram representing a configuration of a power facility management system including a facility state analysis device according to a third embodiment.

FIG. 12 is a diagram representing a configuration of a power facility management system 3 including a facility state analysis device 211.

The power facility management system 3 includes the facility state analysis device 211, a power facility information storage 212, map information storage 213, display 221, and alert unit 222.

The facility state analysis device 211 includes an inputter 251, a calculator 252, a display controller 253, and a remaining life calculator 254.

Here, a configuration and operations of the power facility management system 3 is the same as those of the corresponding configuration units represented in FIG. 1 except for those related to the remaining life calculator 254 and alert unit 222. In the present embodiment, therefore, configuration units different from those of the system represented in FIG. 1 will be described in detail.

The calculator 252 outputs information on an operation period of power facilities of a specific type to the remaining life calculator 254. The calculator 252 further outputs information on a calculated average failure year of the power facilities of that type to the remaining life calculator 254.

The remaining life calculator 254 calculates, as an average remaining life, a value obtained by subtracting the operation period from the average failure year for the specific type of power facility. The remaining life calculator 254 controls the alert unit 222 based at least in part on information on the calculated remaining life.

For example, the remaining life calculator 254 outputs an alert from the alert unit 222 when the calculated remaining life is lower than a predetermined value. As another exemplary configuration, the remaining life calculator 254 may output the information on the calculated remaining life to the alert unit 222 at all times.

The alert unit 222 may be, for example, a buzzer which raises a sound alert or an indicator which indicates a display alert.

Incidentally, the alert unit 222 and display 221 may be configured in integration thereof.

The facility state analysis device 211 according to the present embodiment includes the remaining life calculator 254 which calculates the remaining life of the power facility and performs notification (e.g. alert) based at least in part on the calculated remaining life.

In the power facility management system 3 including the facility state analysis device 211 according to the present embodiment, it is possible to output, for each of the sections, an alert based at least in part on the remaining life of the power facility.

(Fourth Embodiment)

Figure 13:
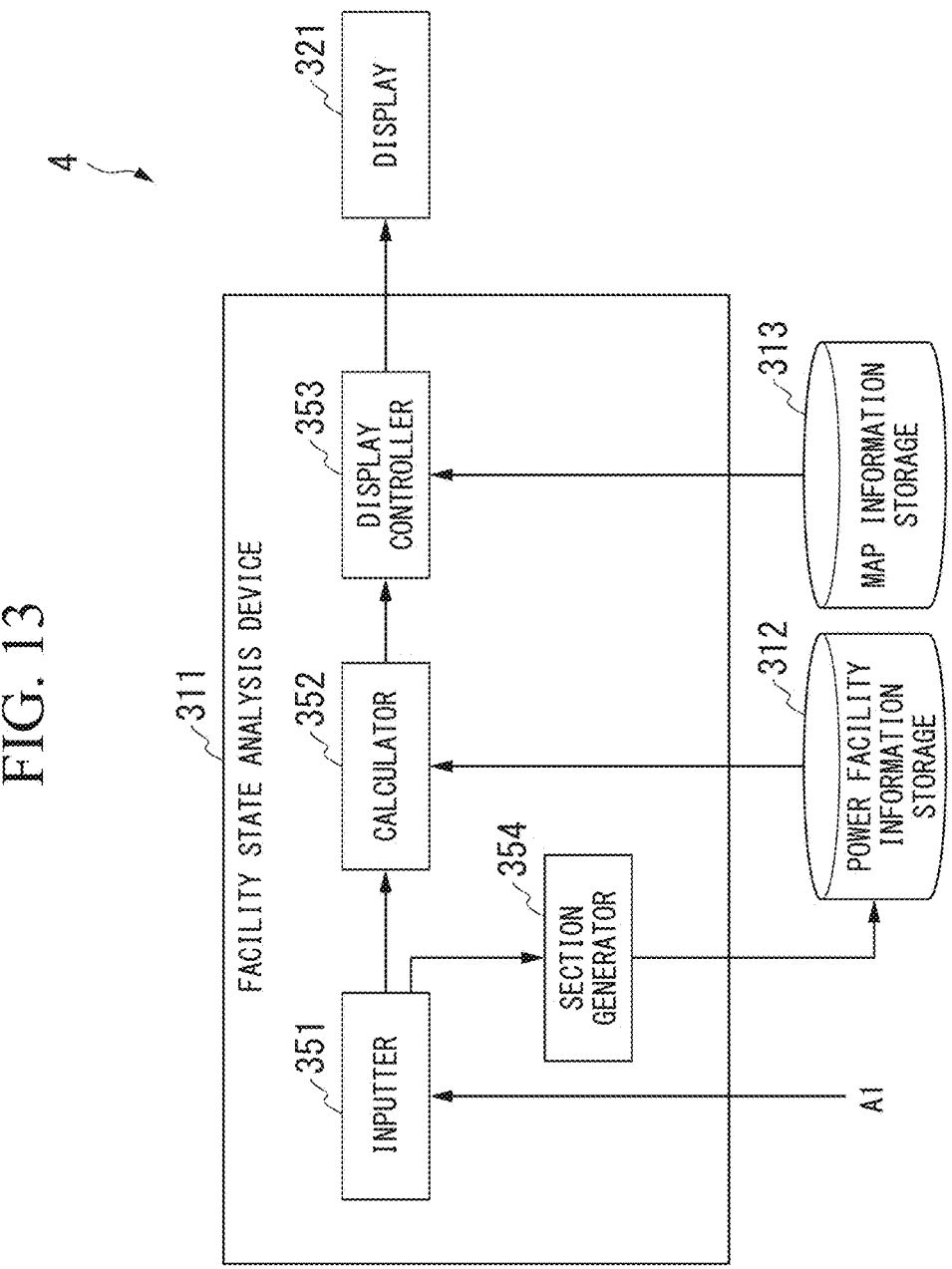
FIG. 13 is a diagram representing a configuration of a power facility management system including a facility state analysis device according to a fourth embodiment.

FIG. 13 is a diagram representing a configuration of a power facility management system 4 including a facility state analysis device 311.

The power facility management system 4 includes the facility state analysis device 311, a power facility information storage 312, map information storage 313, and display 321.

The facility state analysis device 311 includes an inputter 351, a calculator 352, a display controller 353, and a section generator 354.

Here, a configuration and operations of the power facility management system 4 is the same as those of the corresponding configuration units represented in FIG. 1 except for those related to the section generator 354. In the present embodiment, therefore, configuration units different from those of the system represented in FIG. 1 will be described in detail.

The inputter 351 outputs location information of the power facility based at least in part on input information A1 to the section generator 354. This information may be information of power facilities of a specific type or information of a power facility of any type.

The section generator 354 generates information on ranges specifying a plurality of sections based at least in part on the information input from the inputter 351 and reflects the generated information to information stored in the power facility information storage 312. Specifically, the section generator 354 stores, as the information on ranges specifying the sections to which each of the power facilities belong, the generated information in the information stored in the power facility information storage 312. Incidentally, the numerical information representing each of the sections may be, for example, included in the information already stored in the power facility information storage 312 or generated by the section generator 354.

Figure 14:
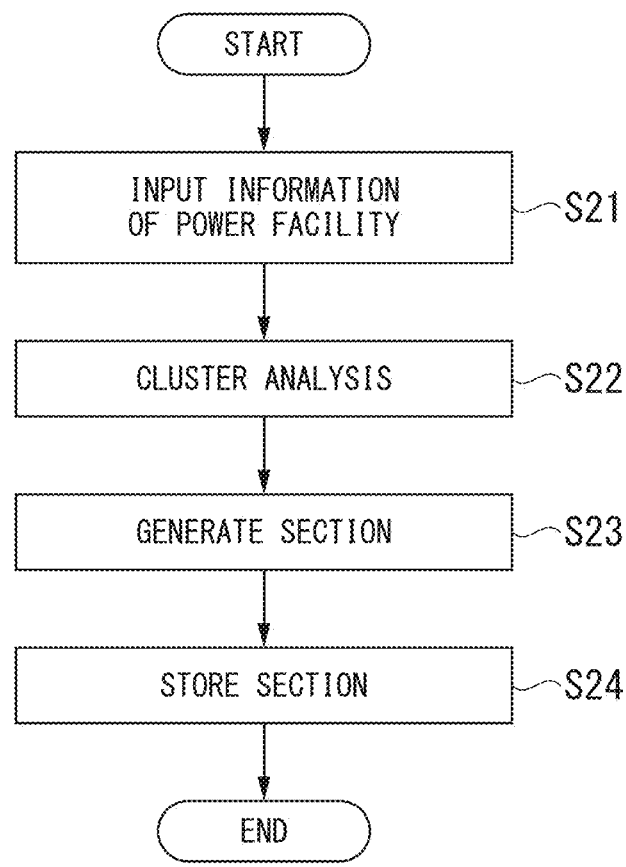
FIG. 14 is a flowchart representing an exemplary procedure of processing performed in a section generator of the facility state analysis device.

FIG. 14 is a flowchart representing an exemplary procedure of processing performed in the section generator 354 of the facility state analysis device 311.

First, the section generator 354 accepts input of information of a power facility accepted by the inputter 351 (step S21). Next, the section generator 354 performs cluster analysis on a distribution of locations of a plurality of power facilities based at least in part on the input information on the power facility (step S22). Next, the section generator 354 generates, for the plurality of sections, information on ranges specifying each of the sections based at least in part on a result of the cluster analysis (step S23). Thereafter, the section generator 354 generates reflects the generated information on the sections to power facility information stored in the power facility information storage 312 (step S24).

Here, the section generator 354 performs cluster analysis, where power facilities closely located with each other are clustered, using location information of the power facilities in the present embodiment. However, as another exemplary configuration, cluster analysis, where power facilities having the same or similar state are clustered, may be performed using location information or information on the state of the power facilities.

Moreover, as the cluster analysis, various methods may be used.

The facility state analysis device 311 according to the present embodiment includes the section generator 354 which generates a section based at least in part on the information accepted by the inputter 351.

In the power facility management system 4 including the facility state analysis device 311 according to the present embodiment, it is possible to generate a plurality of sections based at least in part on a location or state of the power facility.

(Fifth Embodiment)

Figure 15:
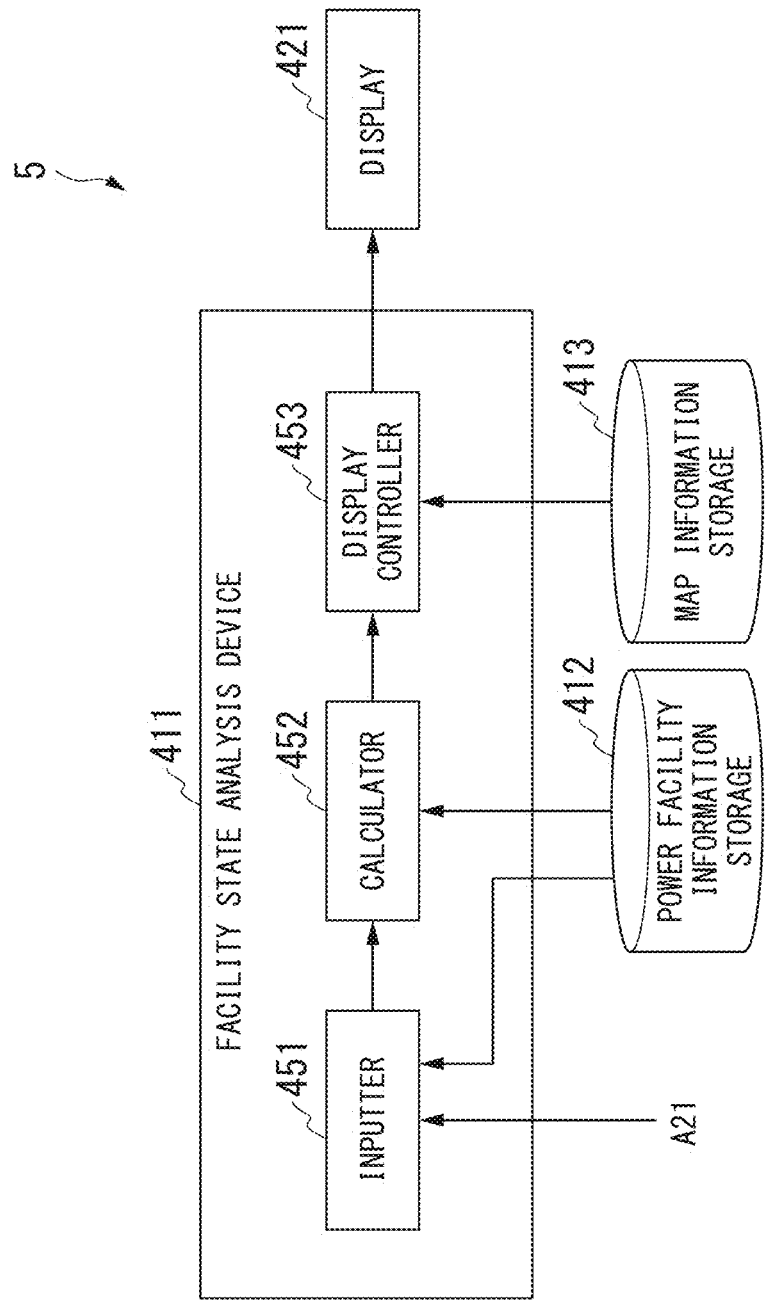
FIG. 15 is a diagram representing a configuration of a power facility management system including a facility state analysis device according to a fifth embodiment.

FIG. 15 is a diagram representing a configuration of a power facility management system 5 including a facility state analysis device 411.

The power facility management system 5 includes the facility state analysis device 411, a power facility information storage 412, map information storage 413, and display 421.

The facility state analysis device 411 includes an inputter 451, a calculator 452, and a display controller 453.

Here, a configuration and operations of the power facility management system 5 is the same as those of the corresponding configuration units represented in FIG. 1 except for those related to the inputter 441 In the present embodiment, therefore, configuration units different from those of the system represented in FIG. 1 will be described in detail.

The inputter 451 accepts input of information A21. The information A21 specifies a state and location of a power facility installed outdoors. In the present embodiment, as the information specifying a location, the ID of the power facility is used. In the present embodiment, the ID and location information of each of the power facilities are associated with each other in the power facility information and thus it is possible to specify a location associated with an ID by using that ID.

The inputter 451 detects the location information of the power facility associated with the accepted ID of the power facility based at least in part on the power facility information stored in the power facility information storage 412. Thereafter, the inputter 451 outputs the accepted information on the state of the power facility and the detected location information of the power facility to the calculator 452.

Here, the inputter 451 detects, from the ID of the power facility, and outputs the location information to the calculator 452 in the present embodiment. However, as another exemplary configuration, the inputter 451 may output the ID of the power facility to the calculator 452 and the calculator 452 may detect, for the input ID of the power facility, the location information of the power facility based at least in part on the power facility information.

In the facility state analysis device 411 according to the present embodiment, the information specifying a location of a power facility is an ID of the power facility. The inputter 451 acquires the location information associated with the ID of the power facility based at least in part on the association information of the ID and location of the power facility.

In the power facility management system 5 including the facility state analysis device 411 according to the present embodiment, it is possible to specify a location of a power facility based at least in part on the ID of the power facility.

(Sixth Embodiment)

Figure 16:
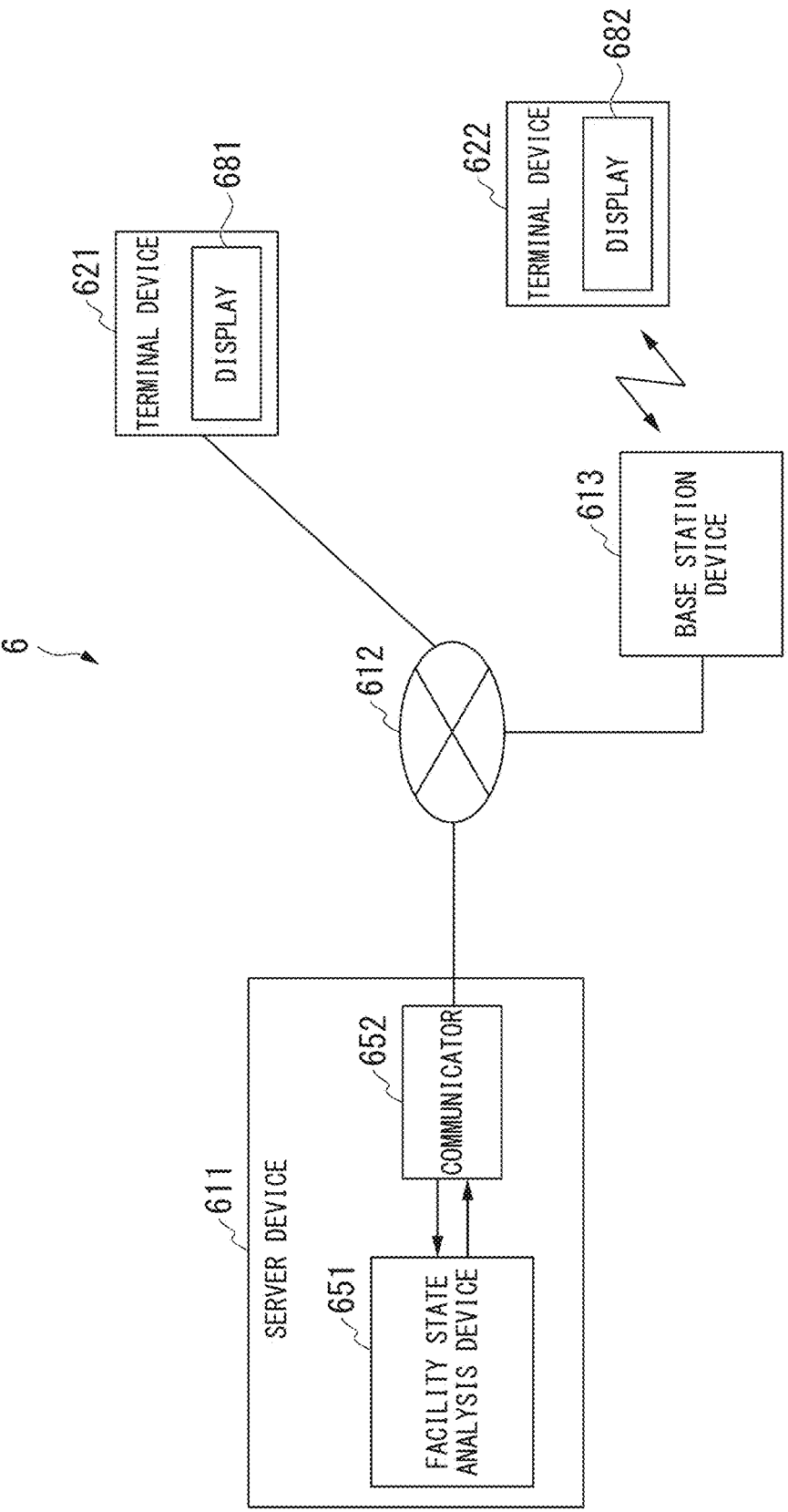
FIG. 16 is a diagram representing a configuration of a power facility management system including a facility state analysis device according to a sixth embodiment.

FIG. 16 is a diagram representing a configuration of a power facility management system 6 including a facility state analysis device 651.

The power facility management system 6 includes a server device 611, a network 612, a base station device 613, a terminal device 621 and a terminal device 622.

The server device 611, base station device 613, and terminal device 621 are connected with each other via the network 612. In the present embodiment, the network 612 is a wired network.

The base station device 613 and terminal device 622 communicate with each other wirelessly.

The terminal devices 621 and 622 include displays 681 and 682, respectively. Each of the terminal devices 621 and 622 may be, for example, devices of mobile terminals such as mobile phone terminals or tablet terminals.

The server device 611 includes the facility state analysis device 651 and a communicator 652.

The facility state analysis device 651 has the same configuration as, for example, any one of those represented in FIGS. 1, 11, 12, 13, and 15.

The server device 611 communicates with the terminal device 621 via the network 612 by the communicator 652.

The server device 611 communicates with the terminal device 622 via the network 612 and base station device 613 by the communicator 652.

The server device 611 is capable of receiving, by the communicator 652, information transmitted from each of the terminal devices 621 and 622 and inputting the information to an inputter of the facility state analysis device 651. This information may be, for example, information on a power facility input by a user or another device to each of the terminal devices 621 and 622.

The server device 611 is capable of transmitting, by the communicator 652, information output from the facility state analysis device 651 to each of the terminal devices 621 and 622. This information may be, for example, display information generated by the facility state analysis device 651. Each of the terminal devices 621 and 622 displays the display information received from the server device 611 on the displays 681 and 682.

In the facility state analysis device 651 according to the present embodiment, a display includes the displays 681 and 682 of the terminal devices 621 and 622.

In the power facility management system 6 including the facility state analysis device 651 according to the present embodiment, management of power facilities can be performed in the form of a cloud system including the server device 611 and terminal devices 621 and 622.

Embodiments of this invention has been described above in detail with reference to drawings. However, a specific configuration is not limited to these embodiments and may include designs within a range not departing from the principals of the invention.

For example, a configuration of a combination of two or more embodiments of the second to sixth embodiments described above may be implemented.

Moreover, the types of power facilities may be various kinds such as a transformer, switch (e.g. high pressure switch), remote controller, disconnector (disconnecting switch), high-tension insulator, low-tension insulator, protective tube for underground wire, instruments, breaker, reinforcement, or concrete column.

Also, the environment attributable to failures of a power facility may include various kinds such as salt (e.g. sea salt), rain, wind, snow, lightning, temperature, exhaust gas, hot spring gas (e.g. sulfur), iron powder along railways, electric corrosion, or vibration.

A specific example may be a case where metal rusts due to salt damage and thereby fails or a case where metal is subjected to fatigue and thereby fails.

Also, failure of a power facility may be, for example, failure of the entire power facility or failure of a predetermined one portion (part) of the power facility. When failure of one portion of the power facility is determined, as an example, determining failure of a portion having a small individual difference (variations) with respect to a period before failure allows for reducing an error between individual power facilities.

Also, when failure of one portion of the power facility is determined, for example, failure of one portion originally included in the power facility may be determined. Alternatively, failure of a part intentionally added the power facility for the purpose of failure determination may be determined. As an example, a part (rust gauge) for confirming the degree of rust may be added to the power facility and failure may be determined based at least in part on the degree of rust in that part.

Incidentally, a program for implementing the facility state analysis device as described above may be stored (recorded) in a computer-readable storage medium (recording medium), thereby allowing a computer system to read the program for execution thereof. As an example, the storage medium is a non-temporary storage medium.

The apparatus, systems and methods in the above-described embodiments may be deployed in part or in whole through machines, a system of circuits, circuitry, hardware processors that executes computer software, software components, program codes, and/or instructions on one or more machines, a system of circuits, circuitry, hardware processors. In some cases, the one or more machines, a system of circuits, circuitry, hardware processors may be part of a general-purpose computer, a server, a cloud server, a client, network infrastructure, mobile computing platform, stationary computing platform, or other computing platform. One or more processors may be any kind of computational or processing device or devices which are capable of executing program instructions, codes, binary instructions and the like. The one or more hardware processors may be or include a signal processor, digital processor, embedded processor, microprocessor or any variants such as a co-processor, for example, math co-processor, graphic co-processor, communication co-processor and the like that may directly or indirectly facilitate execution of program codes or program instructions stored thereon. In addition, the one or more hardware processors may enable execution of multiple programs, threads, and codes. The threads may be executed simultaneously to enhance the performance of the one or more hardware processors and to facilitate simultaneous operations of the application. Program codes, program instructions and the like described herein may be implemented in one or more threads. The one or more hardware processors may include memory that stores codes, instructions and programs as described herein. The machines, a system of circuits, circuitry, hardware processors may access a non-transitory processor-readable storage medium through an interface that may store codes, instructions and programs as described herein and elsewhere. The non-transitory processor-readable storage medium associated with the machines, a system of circuits, circuitry, hardware processors for storing programs, codes, program instructions or other type of instructions capable of being executed by the computing or processing device may include but may not be limited to one or more of a memory, hard disk, flash drive, RAM, ROM, CD-ROM, DVD, cache and the like.

A processor may include one or more cores that may enhance speed and performance of a multiprocessor. In some embodiments, the process may be a dual core processor, quad core processors, other chip-level multiprocessor and the like that combine two or more independent cores.

The methods, apparatus and systems described herein may be deployed in part or in whole through a machine that executes computer software on a server, client, firewall, gateway, hub, router, or other such computer and/or networking hardware.

The software program may be associated with one or more client that may include a file client, print client, domain client, internet client, intranet client and other variants such as secondary client, host client, distributed client and the like. The client may include one or more of memories, processors, computer readable media, storage media, physical and virtual ports, communication devices, and interfaces capable of accessing other clients, servers, machines, and devices through a wired or a wireless medium, and the like. The programs or codes as described herein may be executed by the client. In addition, other devices required for execution of methods as described in this application may be considered as a part of the infrastructure associated with the client. The client may provide an interface to other devices including servers, other clients, printers, database servers, print servers, file servers, communication servers, distributed servers and the like. This coupling and/or connection may facilitate remote execution of program across the network. The networking of some or all of these devices may facilitate parallel processing of a program or method at one or more location. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The software program may be associated with one or more servers that may include a file server, print server, domain server, internet server, intranet server and other variants such as secondary server, host server, distributed server and the like. The server may include one or more of memories, processors, computer readable media, storage media, physical and virtual ports, communication devices, and interfaces capable of accessing other servers, clients, machines, and devices through a wired or a wireless medium, and the like. The methods, programs or codes as described herein may be executed by the server. In addition, other devices required for execution of methods as described in this application may be considered as a part of the infrastructure associated with the server. The server may provide an interface to other devices including clients, other servers, printers, database servers, print servers, file servers, communication servers, distributed servers, social networks, and the like. This coupling and/or connection may facilitate remote execution of program across the network. The networking of some or all of these devices may facilitate parallel processing of a program or method at one or more locations. Any of the devices attached to the server through an interface may include at least one storage medium capable of storing programs, codes and/or instructions. A central repository may provide program instructions to be executed on different devices. In this implementation, the remote repository may act as a storage medium for program codes, instructions, and programs.

The methods, apparatus and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing devices associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions described herein may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, programs codes, and instructions described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory, for example, USB sticks or keys, floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or or intangible items from one state to another. The methods and systems described herein may also transform data representing physical and/or intangible items from one state to another.

The modules, engines, components, and elements described herein, including in flow charts and block diagrams throughout the figures, imply logical boundaries between the modules, engines, components, and elements. However, according to software or hardware engineering practices, the modules, engines, components, and elements and the functions thereof may be implemented on one or more processors, computers, machines through computer executable media, which are capable of executing program instructions stored thereon as a monolithic software structure, as standalone software modules, or as modules that employ external routines, codes, services, or any combination of these, and all such implementations may be within the scope of the present disclosure. Examples of such machines may include, but is not limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers, processor-embedded eyewear and the like. Furthermore, the modules, engines, components, and elements in the flow chart and block diagrams or any other logical component may be implemented on one or more machines, computers or processors capable of executing program instructions. Whereas the foregoing descriptions and drawings to which the descriptions have been referred set forth some functional aspects of the disclosed systems, no particular arrangement of software for implementing these functional aspects should be inferred from these descriptions unless explicitly stated or otherwise clear from the context. It will also be appreciated that the various steps identified and described above may be varied, and that the order of steps may be adapted to particular applications of the techniques disclosed herein. All such variations and modifications are intended to fall within the scope of this disclosure. The descriptions of an order for various steps should not be understood to require a particular order of execution for those steps, unless required by a particular application, or explicitly stated or otherwise clear from the context.

The methods and/or processes described above, and steps thereof, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

As used herein, the following directional terms "front, back, above, downward, right, left, vertical, horizontal, below, transverse, row and column" as well as any other similar directional terms refer to those instructions of a device equipped with embodiments of the present invention. Accordingly, these terms, as utilized to describe embodiments of the present invention should be interpreted relative to a device equipped with embodiments of the present invention.

Each element for the system, device and apparatus described above can be implemented by hardware with or without software. In some cases, the system, device and apparatus may be implemented by one or more hardware processors and one or more software components wherein the one or more software components are to be executed by the one or more hardware processors to implement each element for the system, device and apparatus. In some other cases, the system, device and apparatus may be implemented by a system of circuits or circuitry configured to perform each operation of each element for the system, device and apparatus.

While the present disclosure includes many embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A power facility management method, comprising:
examining, for each type of a plurality of different types of power facilities, each of the power facilities which was installed outdoors and has been placed in use over a plurality of years, wherein each of the power facilities is examined in terms of whether the power facility is at least in part in failure;
obtaining, for each of the plurality of different types of power facilities, i) information specifying a respective state of each power facility examined and ii) information specifying a respective location of installation of each power facility over a map having a plurality of sections;
performing statistical processing, using at least one hardware processor, a) for each type of the plurality of different types of power facilities and b) for each section of the map, based at least in part on i) the information specifying the respective state of each power facility examined, ii) information specifying the respective location of installation of each power facility over the map having the plurality of sections, and iii) information on the plurality of sections on the map, by processing power-facility-related information;
determining, using at least one hardware processor, a) for each section on the map and b) for each type of the plurality of different types of power facilities, a respective average failure year of the power facilities based at least in part on the performed statistical processing; and
making, using at least one hardware processor, a) for each section on the map and b) for each type of the plurality of different types of power facilities, a display device display the determined respective average failure year of the power facilities.

2. The power facility management method according to claim 1, wherein the plurality of different types of power facilities are fatigue-damageable dependent upon outdoor environmental conditions.

3. The power facility management method according to claim 2, wherein the plurality of different types of power facilities are fatigue-damageable by wind or by rust caused due to humidity and salt.

4. The power facility management method according to claim 1,
wherein each power facility of the plurality of different types of power facilities was installed outdoors at the respective location and then removed from the respective location.

5. The power facility management method according to claim 1, further comprising:
classifying the average failure year into a predetermined number of ranges,
wherein making the display device display the average failure year comprises making the display device display the average failure year superimposed on the map.

6. The power facility management method according to claim 1, wherein making the display device display the average failure year comprises making, for each of regions smaller than the section, the display device display the average failure year, superimposed on the map.

7. The power facility management method according to claim 1, wherein making the display device display the average failure year comprises making the display device display the average failure year and a distance from a coast, superimposed on the map.

8. The power facility management method according to claim 1, wherein determining, a) for each section on the map and b) for each type of the plurality of different types of power facilities, the respective average failure year of the power facilities is further based at least in part on a Weibull analysis.

* * * * *